(12) United States Patent
Keum

(10) Patent No.: US 12,270,698 B2
(45) Date of Patent: Apr. 8, 2025

(54) HEIGHT MEASURER AND WEIGHT MEASUREMENT DEVICE

(71) Applicant: INBODY CO., LTD., Seoul (KR)

(72) Inventor: Dong Hoon Keum, Seoul (KR)

(73) Assignee: INBODY CO., LTD., Seoul (KR)

( * ) Notice: Subject to any disclaimer, the term of this patent is extended or adjusted under 35 U.S.C. 154(b) by 861 days.

(21) Appl. No.: 17/422,903

(22) PCT Filed: Mar. 14, 2019

(86) PCT No.: PCT/KR2019/002935
§ 371 (c)(1),
(2) Date: Mar. 14, 2022

(87) PCT Pub. No.: WO2020/149453
PCT Pub. Date: Jul. 23, 2020

(65) Prior Publication Data
US 2022/0205831 A1 Jun. 30, 2022

(30) Foreign Application Priority Data
Jan. 14, 2019 (KR) .................. 10-2019-0004890

(51) Int. Cl.
*G01G 19/50* (2006.01)
(52) U.S. Cl.
CPC .................. *G01G 19/50* (2013.01)
(58) Field of Classification Search
CPC .................. G01G 19/50; A61B 5/103
(Continued)

(56) References Cited

U.S. PATENT DOCUMENTS 6,327,494 B1 12/2001 Sakai
8,648,267 B2 * 2/2014 Honda ................ G01G 21/244
177/DIG. 9
(Continued)

FOREIGN PATENT DOCUMENTS

CN 206798323 U 12/2017
JP 07075625 A 3/1995
(Continued)

OTHER PUBLICATIONS

International Search Report and Written Opinion Form PCT/ISA/210 and PCT/ISA/237, International Application No. PCT/KR2019/002935, pp. 1-9 International Filing Date Mar. 14, 2019, mailing date of search report Oct. 16, 2019.
(Continued)

*Primary Examiner* — Jacques M Saint Surin
(74) *Attorney, Agent, or Firm* — BOND, SCHOENECK & KING, PLLC; George R. McGuire

(57) ABSTRACT

Disclosed are a height measurer and a weight measurement device. The disclosed height measurer comprises: a bottom plate; a standing frame which is connected to the bottom plate and supported thereby, and has a rail on the rear surface portion thereof; a moving part that moves up and down along the rail; a tact switch disposed on at least a portion of the moving part; and a head plate which surrounds the standing frame, moves up and down along with the moving part, is hinge-coupled to the moving part, and applies a pressing force to the tact switch while being lifted up upon coming into contact with the head of a user during height measurement.

10 Claims, 11 Drawing Sheets

(58) Field of Classification Search
USPC .......................................................... 177/245
See application file for complete search history.

(56) References Cited

U.S. PATENT DOCUMENTS

| | | | |
|---|---|---|---|
| 9,316,475 B2* | 4/2016 | Liu ....................... | A61B 5/1072 |
| 10,775,155 B2* | 9/2020 | Zheng .................... | G01B 3/008 |
| 2011/0024202 A1* | 2/2011 | Chen ....................... | G01G 19/44 |
| | | | 177/245 |

FOREIGN PATENT DOCUMENTS

| KR | 1019980008172 A | 4/1998 |
|---|---|---|
| KR | 19990005461 U | 2/1999 |
| KR | 20010019513 A | 3/2001 |
| KR | 200356627 Y1 | 7/2004 |
| KR | 1020100119363 A | 11/2010 |
| KR | 1020180122060 A | 11/2018 |
| WO | 8707019 A1 | 11/1987 |

OTHER PUBLICATIONS

Translated Chinese office action, Application No. 201980093735.4, dated Jan. 19, 2024.
Translated Chinese Office Action, App. No. 201980093735.4, dated Aug. 6, 2024, entire document.

* cited by examiner

HEIGHT MEASURER AND WEIGHT MEASUREMENT DEVICE

TECHNICAL FIELD

Example embodiments relate to a height measurer and a weight measurement device, and more particularly, to a height measurer using a standing frame having a rail on a rear surface portion thereof and a head plate having a lopsided center of gravity, and to a weight measurement device using a supporter including a plurality of bridges configured to vertically transfer a force to a neck portion of a load cell.

BACKGROUND ART

Height and weight measurements are performed in various places including, for example, hospitals, schools, homes, and companies for various purposes. The height measurement is performed to determine a height of a user by measuring the height while the user is standing upright. The weight measurement is performed to determine a weight of a user by measuring a force of the user pressing a bottom plate on which the user is standing for the measurement.

For the height measurement, a height measurer is used. However, a rail for an upward and downward movement of a head plate of the height measurer is disposed on a front side of a standing stand of the height measurer, which may degrade visual aesthetics. In addition, a display is disposed on a side surface of the standing stand, which may limit the installation space for the height measurer. For the weight measurement, when a bottom plate is disposed on an inclined surface, a force pressed by a weight of a user may not be correctly transferred, which may lead to the occurrence of an error in the measurement.

DISCLOSURE OF THE INVENTION

Technical Goals

An aspect provides a height measurer that may have an aesthetic effect while maintaining a high level of accuracy in a measurement, using a standing frame having a rail on a rear surface portion thereof and using a head plate that is returned by its own weight after applying a pressing force to a tact switch while being lifted upward upon coming into contact with a head of a user due to the center of gravity lopsided to a front portion thereof during a height measurement.

Another aspect provides a weight measurement device that may measure a weight of a user with a relatively high level of accuracy as a plurality of bridges of a supporter connected to a load cell are bent independently, even when an axial bottom on which the supporter stands on a floor and a pressing direction in which a neck portion of the load cell is pressed by the user do not correspond to each other.

Still another aspect provides a height measurer and a weight measurement device that, when a preset condition is satisfied, may display a measurement result in a second direction changed from a first direction, and may thus allow a user who is a measurement target or a supervisor who manages and supervises a measurement process to readily verify the measurement result.

Yet another aspect provides a height measurer and a weight measurement device including a head plate that may stand by at a suitable height based on whether a measurement target is an adult or a child by waiting at a first height or a second height, and may thus provide a more effective measurement process.

Technical Solutions

According to an example embodiment, there is provided a height measurer including a bottom plate, a standing frame connected to the bottom plate to be supported thereby and having a rail on a rear surface thereof, a moving portion configured to vertically move the rail, a tact switch disposed in at least a portion of the moving portion, and a head plate surrounding the standing frame, configured to move vertically along the moving portion, hinge-coupled to the moving portion, and configured to apply a pressing force to the tact switch while being lifted upward upon coming into contact with a head of a user during a height measurement.

The head plate may be a panel having a center of gravity lopsided toward a front portion compared to a rear portion thereof, and be restored not to press the tact switch by its own weight when it is not in a state of being lifted upward.

The head plate may have a curved shape designed to allow the center of gravity to be lopsided.

A front surface of the standing frame may be formed as a flat plate, and the rear surface of the standing frame may include a groove on which the rail is disposed.

While the measurement is not being performed, the head plate may stand by at a first height in a first set state, and stand by at a second height lower than the first height in a second set state.

The bottom plate may include a display configured to display a measurement result which is a result of the measurement performed on the user. The display may display the measurement result in a first direction, and then in a second direction different from the first direction when a preset condition is satisfied.

The preset condition may be at least one of a condition that a first threshold time elapses after the tact switch is restored after being pressed, a condition that a second threshold time elapses after the measurement is terminated, a condition that a third threshold time elapses after a weight change is detected as the user steps down from the bottom plate, and a condition that a separate operation command is received.

The height measurer may further include a load cell attached to a rear surface of the bottom plate and configured to measure a weight of the user as a neck portion thereof is bent, and a supporter configured to support the bottom plate from a floor and configured to transfer, to the load cell, a pressing force of the user standing on the bottom plate.

Even when an axial direction in which the supporter stands on the floor and a pressing direction in which the neck portion is pressed by the user do not correspond to each other during the measurement, the supporter may apply a pressure to the load cell in a direction in which the neck portion of the load cell is bent than the axial direction, as a plurality of legs of the supporter is bent independently from each other.

According to another example embodiment, there is provided a weight measurement device including a bottom plate on which a user steps up, a load cell attached to a rear surface of the bottom plate and configured to measure a weight of the user as a neck portion thereof is bent, and a supporter configured to support the bottom plate from a floor and configured to transfer, to the load cell, a pressing force of the user standing on the bottom plate.

Even when an axial direction in which the supporter stands on the floor and a pressing direction in which the neck portion is pressed by the user do not correspond to each other during the measurement, the supporter may apply a pressure to the load cell in a direction in which the neck portion of the load cell is bent than the axial direction, as a plurality of bridges of the supporter is bent independently from each other.

Each of the bridges of the supporter may have a spiral shape that connects, in the supporter, a first portion connected to the load cell and a second portion connected to the floor.

Each of the bridges of the supporter may include a first fixing portion fixed to the first portion connected to the floor in the supporter, a second fixing portion fixed to the second portion connected to the load cell, and a connecting portion configured to connect the first fixing portion and the second fixing portion to be in a structure parallel to a circumference of the second portion.

Effects

According to an example embodiment described herein, it is possible to have an aesthetic effect while maintaining a high level of accuracy in a measurement, using a standing frame having a rail on a rear surface portion thereof and using a head plate that is returned by its own weight after applying a pressing force to a tact switch while being lifted upward upon coming into contact with a head of a user due to the center of gravity lopsided to a front portion thereof during a height measurement.

According to an example embodiment described herein, it is possible to measure a weight of a user with a relatively high level of accuracy as a plurality of bridges of a supporter connected to a load cell are bent independently, even when an axial bottom on which the supporter stands on a floor and a pressing direction in which a neck portion of the load cell is pressed by the user do not correspond to each other.

According to an example embodiment described herein, it is possible to, when a preset condition is satisfied, display a measurement result in a second direction changed from a first direction, thereby allowing a user who is a measurement target or a supervisor who manages and supervises a measurement process to readily verify the measurement result.

According to an example embodiment described herein, as a head plate may stand by at a suitable height based on whether a measurement target is an adult or a child by waiting at a first height or a second height, it is thus possible to provide a more effective measurement process.

BEST MODE FOR CARRYING OUT THE INVENTION

Figure 1:
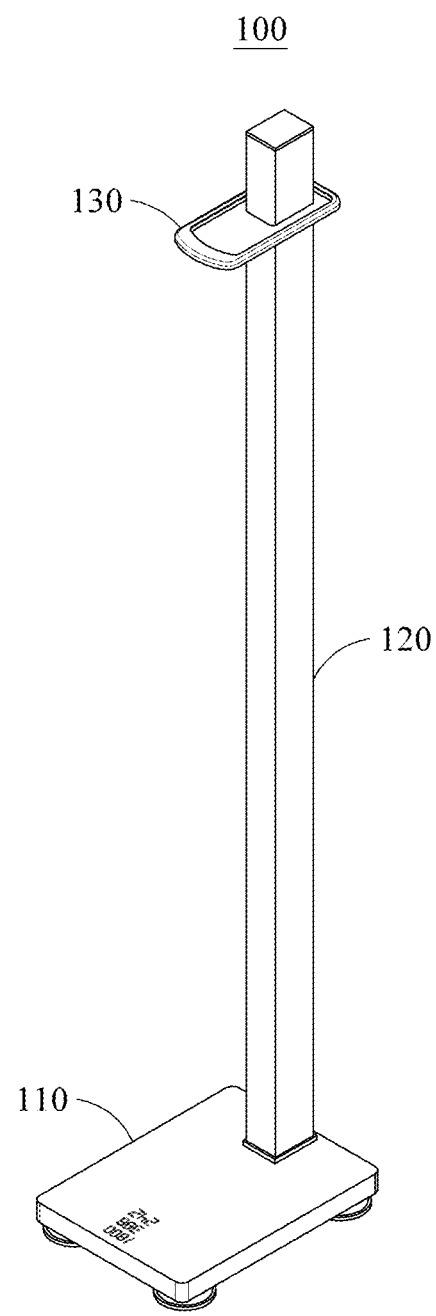
FIG. 1 is a perspective view of a height measurer according to an example embodiment.

Hereinafter, some examples will be described in detail with reference to the accompanying drawings. However, various alterations and modifications may be made to the examples. Here, the examples are not construed as limited to the disclosure and should be understood to include all changes, equivalents, and replacements within the idea and the technical scope of the disclosure.

Although terms such as "first," "second," and "third" may be used herein to describe various members, components, regions, layers, or sections, these members, components, regions, layers, or sections are not to be limited by these terms. Rather, these terms are only used to distinguish one member, component, region, layer, or section from another member, component, region, layer, or section.

Throughout the specification, when a component is described as being "connected to" or "coupled to" another component, it may be directly "connected to" or "coupled to" the other component, or there may be one or more other components intervening therebetween. In contrast, when an element is described as being "directly connected to" or "directly coupled to" another element, there can be no other elements intervening therebetween.

The terminology used herein is for the purpose of describing particular examples only and is not to be limiting of the examples. As used herein, the singular forms "a," "an," and "the" are intended to include the plural forms as well, unless the context clearly indicates otherwise. It will be further understood that the terms "comprises/comprising" and/or "includes/including" when used herein, specify the presence of stated features, integers, steps, operations, elements, and/or components, but do not preclude the presence or addition of one or more other features, integers, steps, operations, elements, components and/or groups thereof.

Unless otherwise defined, all terms, including technical and scientific terms, used herein have the same meaning as commonly understood by one of ordinary skill in the art to which this disclosure pertains based on an understanding of the present disclosure. Terms, such as those defined in commonly used dictionaries, are to be interpreted as having a meaning that is consistent with their meaning in the context of the relevant art and the present disclosure, and are not to be interpreted in an idealized or overly formal sense unless expressly so defined herein.

Also, in the description of example embodiments, detailed description of structures or functions that are thereby known after an understanding of the disclosure of the present application will be omitted when it is deemed that such description will cause ambiguous interpretation of the example embodiments. Hereinafter, examples will be described in detail with reference to the accompanying drawings, and like reference numerals in the drawings refer to like elements throughout.

FIG. 1 is a perspective view of a height measurer according to an example embodiment.

Referring to FIG. 1, a height measurer 100 includes a bottom plate 110, a standing frame 120, a moving portion, a tact switch, and a head plate 130. The height measurer 100 may measure a height of a user standing on the bottom plate 110. The height measurer 100 may also measure a weight of the user standing on the bottom plate 110.

The bottom plate 110 may be a portion on which the user, a measurement target, steps up to stand thereon. Although to be described in detail later, the weight of the user may be measured through a load cell and a supporter disposed on a rear surface of the bottom plate 110.

The standing frame 120 may be connected to the bottom plate 110 to be supported thereby, and have a rail on a rear surface thereof. A front surface of the standing frame 120 may be formed of a flat plate, and the rear surface of the standing frame 120 may include a groove in which the rail may be disposed. As the rail is disposed on the rear surface, instead of the front surface of the standing frame 120, it is possible to achieve an aesthetic effect.

Although not illustrated in FIG. 1, the moving portion may vertically move the rail disposed on the rear surface of the standing frame 120. In addition, although not illustrated in FIG. 1, the tact switch may be disposed in at least a portion of the moving portion.

The head plate 130 may surround the standing frame 120 and move up and down along the moving portion, and be hinge-coupled to the moving portion to apply a pressing force to the tact switch while being lifted upwards after contacting a head of the user during a height measurement. Although to be described in detail later, the head plate 130 may be a curved panel having a center of gravity lopsided toward a front portion compared to a rear portion thereof.

According to an example embodiment, the head plate 130 may move downward along the moving portion when the user steps up on the bottom plate 110, after being on standby at a position higher than the height of the user before the user who is a target for the height measurement stands on the bottom plate 110. The head plate 130 may touch the head of the user and return to its original position, and the height of the user may be measured based on a height at which the head of the user is touched. As the head of the user is touched, the head plate 130 may apply a pressing force to the tact switch, which will be further described hereinafter.

For example, in a case in which the measurement target is a child whose height is smaller than that of an adult, a distance that the head plate 130 needs to move downward from a standby position to touch a head of the child may be great, and accordingly a time used for moving downward may increase. Thus, the standby position of the head plate 130 may need to be changed based on the measurement target. For example, during a time that is not for the measurement, the head plate 130 may stand by at a first height in a first set state, and the head plate 130 may stand by at a second height lower than the first height in a second set state. In this example, the first set state may indicate a state in which the measurement target is set as an adult, and the second set state may indicate a state in which the measurement target is set as a child. For example, the first height may be 2 meters (m) and the second height may be 1.8 m, but examples are not limited thereto. For example, various heights may be applied to the first height and the second height without limitation.

FIGS. 2 through 5 are diagrams illustrating a head plate according to an example embodiment.

Figure 2:
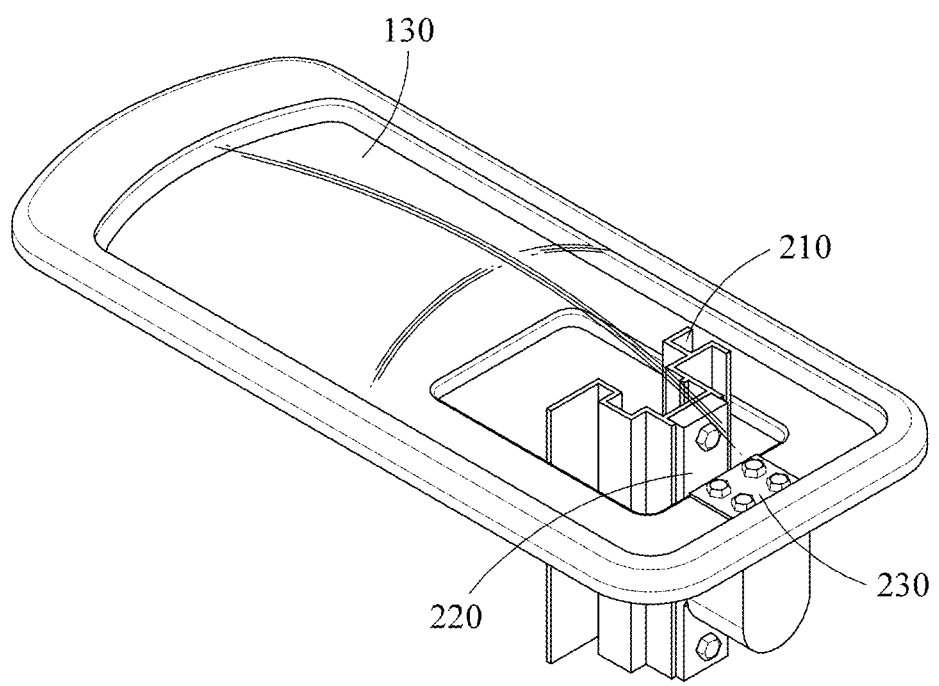
FIGS. 2 through 5 are diagrams illustrating a head plate according to an example embodiment.

FIG. 2 is a perspective view of the head plate 130 according to an example embodiment. The head plate 130 may be a panel having a center of gravity lopsided toward a front portion thereof, compared to a rear portion thereof. When it is not lifted upward after touching a head of a user during a height measurement, the head plate 130 may be restored so as not to press a tact switch by its own weight. In FIG. 2, an upper left portion may correspond to the front portion, and a lower right portion may correspond to the rear portion. For example, the head plate 130 may have a curved shape designed such that the center of gravity is lopsided.

A hole may be formed in the rear portion of the head plate 130. As a standing frame is disposed in the hole, the head plate 130 may move vertically along the standing frame. For the convenience of description, only a rail 210 disposed on a rear surface of the standing frame is illustrated in FIG. 2, and a moving portion 220 may move the rail 210 upward and downward.

A head stopper bracket 230 may restrict the movement of the head plate 130. For example, the head stopper bracket 230 may restrict the movement of the head plate 130 such that the head plate 130 does not rotate by more than a preset angle when the head plate 130 is lifted upward by being in contact with the head of the user. In addition, the head stopper bracket 230 may maintain a state in which the head plate 130 is parallel to the ground by restricting the head plate 130 not to rotate by more than a preset angle when the head plate 130 is returned to its original position by its own weight while not being in contact with the head of the user.

Figure 3:
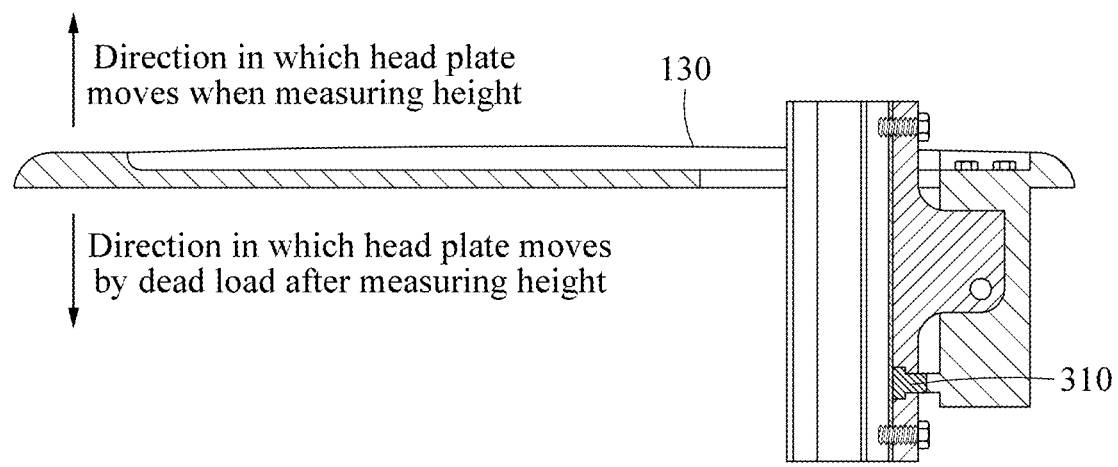

FIG. 3 is a side view of the head plate 130 according to an example embodiment.

As described above, the head plate 130 may be provided in the form in which a rear portion thereof surrounds a standing stand and a front portion thereof touches a head of a user head during a height measurement. While the head plate 130 is being lifted upward when the front portion of the head plate 130 touches the head of the user during the height measurement, the rear portion of the head plate 130 may apply a pressing force to a tact switch 310. The height measurer may measure a height of the user based on a height of the head plate 130 from which the tact switch 310 is sensed as being pressed. The head plate 130 may be restored to its original position so as not to press the tact switch 310 by its own weight after the height measurement.

Figure 4:
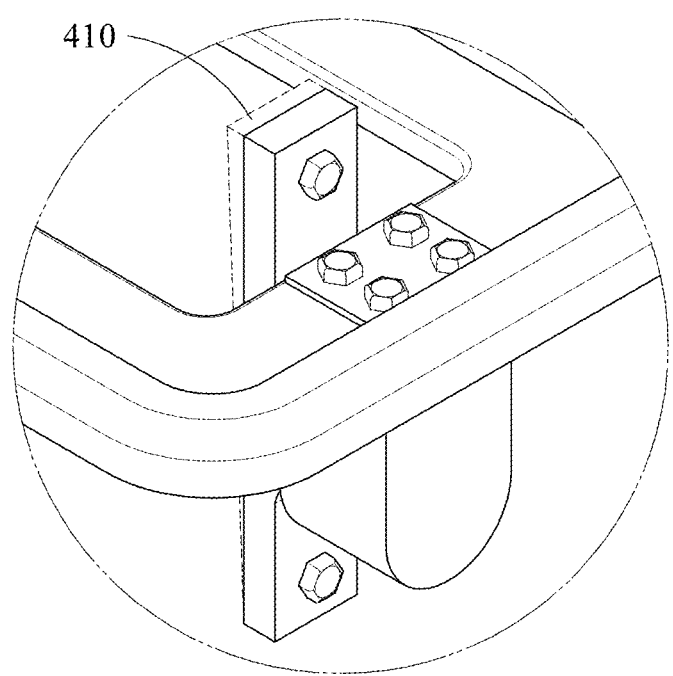

FIG. 4 is an enlarged view of a portion 410 of the head plate 130 that is brought into contact with a moving portion according to an embodiment. The portion 410 may be added to the head plate 130 to prevent the head plate 130 from being inclined as a center of gravity of the head plate 130 is lopsided. For example, the portion 410 may be provided in a structure in which an upper surface is wider than a lower surface, such that the head plate 130 is kept horizontal or parallel.

Figure 5:
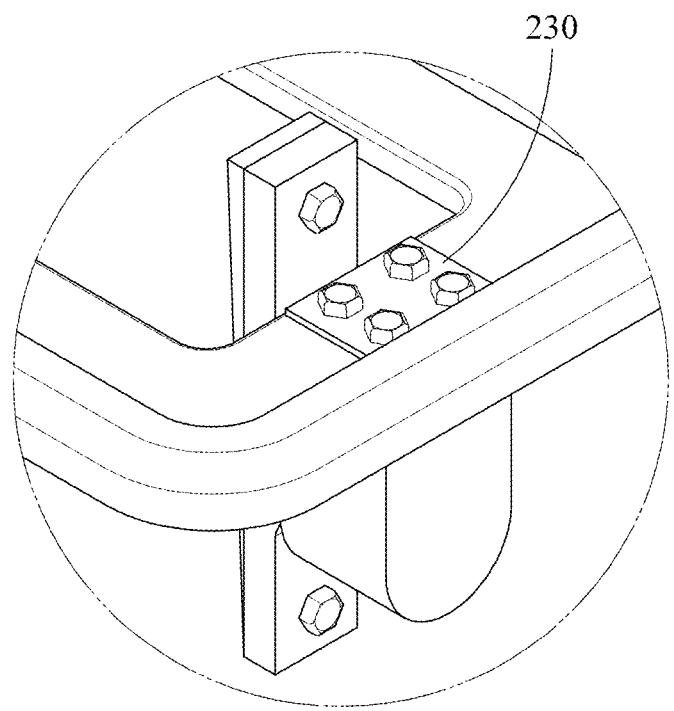

FIG. 5 is an enlarged view of the head stopper bracket 230 for restricting a movement of the head plate 130 according to an embodiment.

Figure 6:
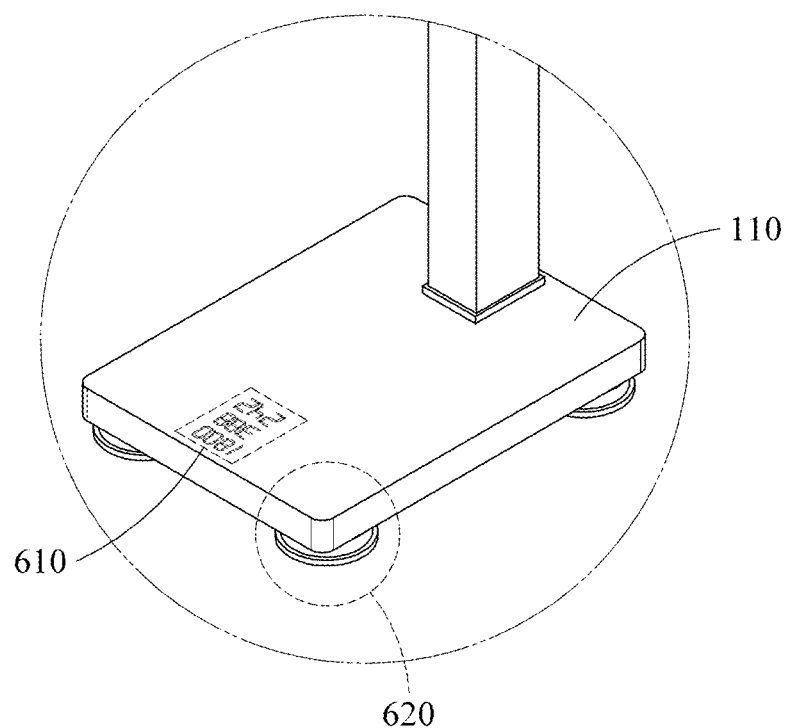
FIG. 6 is a perspective view of a bottom plate according to an example embodiment.

FIG. 6 is an enlarged view of the bottom plate 110 according to an example embodiment.

Referring to FIG. 6, the bottom plate 110 includes a display 610 configured to display a measurement result. For example, the measurement result may include at least one of a height and a weight of a user. The display 610 is included in the bottom plate 110, and it is thus possible to minimize a limitation of a space in which the height measurer may be disposed.

The display 610 may control a direction in which the measurement result is displayed. For example, the display 610 may display the measurement result in a second direction that is different from a first direction when a preset condition is satisfied while displaying the measurement result in the first direction. For example, the first direction indicates a direction in which the user who steps up on the bottom plate 110 with his/her back against a standing stand may readily read the measurement result. The second direction indicates a reverse direction of the first direction, which is a direction in which a supervisor who manages and/or supervises a measurement process may readily read the measurement result while standing facing the user, or a direction in which the user who has completed the measurement may readily read the measurement result after coming down from the bottom plate 110. However, examples of the first direction and the second direction are not limited to the foregoing example, and various other examples may be applied without limitation.

The preset condition may include at least one of a condition that a first threshold time elapses after a tact switch is pressed and then restored, a condition that a second threshold time elapses after the measurement is finished, a condition that a third threshold time elapses after a weight change is sensed as a user comes down from a bottom plate, and a condition that a separate operation command is received. Each of the threshold times may include a time that is greater than or equal to 0 second, but various times may be applied without limitation.

For example, in the case of the condition that the first threshold time elapses after the tact switch is pressed and restored, based on a reference time after the first threshold time from a point in time at which a head plate touching a head of a user moves upward along a moving portion and is restored not to press a tact switch by its own weight, the measurement result may be displayed in the first direction before the reference time and then be displayed in the second direction after the reference time.

For another example, in the case of the condition that the second threshold time elapses after the measurement is finished, the measurement result may include at least one of a height measurement result and a weight measurement result. In the case of a height measurement, the height measurer may determine a height of a user based on a position at which the tact switch is pressed. Based on a reference time after the second threshold time from a point in time at which the height is determined, the measurement result which is the height of the user may be displayed in the first direction before the reference time, and then be displayed in the second direction after the reference time. In addition, in the case of a weight measurement, based on a reference time after the second threshold time from a point in time at which a weight of a user standing on the bottom plate is measured, the measurement result which is the weight of the user may be displayed in the first direction before the reference time, and then be displayed in the second direction after the reference time. Alternatively, when both the height measurement and weight measurement are applied, based on a reference time after the second threshold time from a point in time at which both height and weight of a user are measured, the measurement result which is the height and the weight of the user may be displayed in the first direction before the reference time, and then be displayed in the second direction after the reference time.

For still another example, in the case of the condition that the third threshold time elapses after a weight change is sensed as a user comes down from the bottom plate, the user may come down from the bottom plate when the measurement is finished, which may be sensed as the weight change. Based on a reference time after the third threshold time from a point in time at which the weight change is sensed, the measurement result may be displayed in the first direction before the reference time and then be displayed in the second direction after the reference time.

For yet another example, in the case of the condition that a separate operation command is received, an operation command for a display direction of the measurement result may be input from a user who is a measurement target or a supervisor who manages or supervises a measurement process. The measurement result may be displayed in a direction according to the input operation command.

FIGS. 7 through 11 are diagrams illustrating a load cell and a supporter according to an example embodiment.

Figure 7:
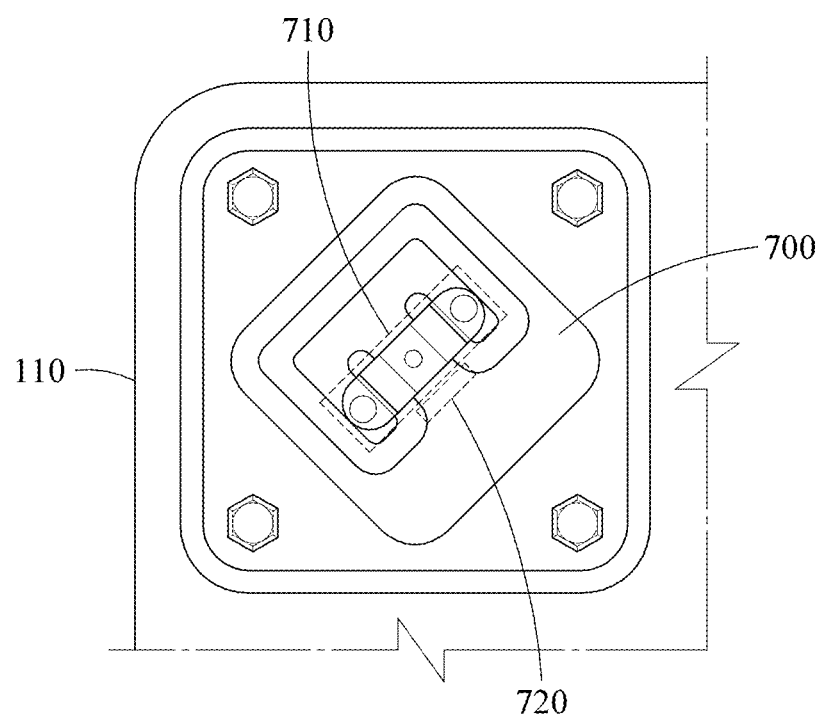
FIGS. 7 through 11 are diagrams illustrating a load cell and a supporter according to an example embodiment.

FIG. 7 illustrates a load cell 700 disposed under the bottom plate 110 according to an example embodiment.

According to an example embodiment, the load cell 700 may be disposed at each of four vertex portions (see 620 in FIG. 6) of the bottom plate 110, and each load cell 700 includes a force transfer portion 710 and a neck portion 720. The load cell 700 may be a sensor configured to measure a physical quantity such as a force or load. When a force is applied to a load cell, an electric signal corresponding to the force applied to the load cell may be generated, and a weight may be determined based on the generated electric signal. For example, when a force is applied to the force transfer portion 710 by a weight of a user, the force transfer portion 710 may transfer the applied force to the neck portion 720, and the neck portion 720 may be bent by the transferred force. The amount of bending of the neck portion 720 may be measured by a strain gauge, and the weight of the user may thereby be determined.

Figure 8:
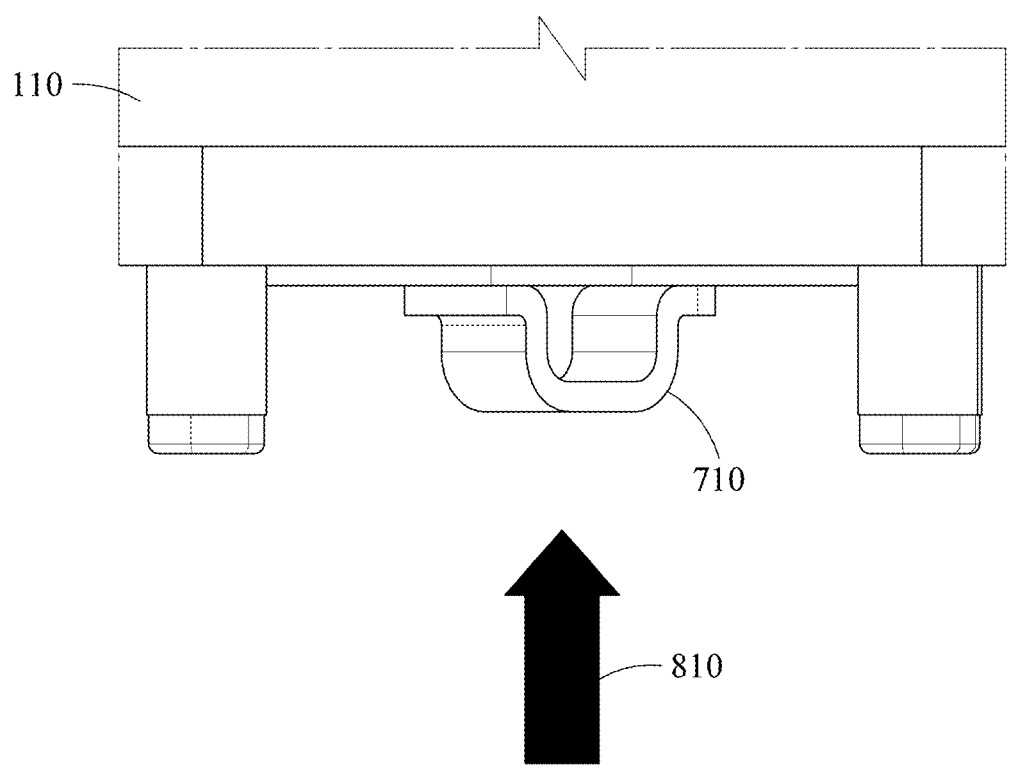

FIG. 8 is a side view of the load cell 700 according to an example embodiment. A force 810 by a weight of a user may be applied to the force transfer portion 710.

Figure 9A:
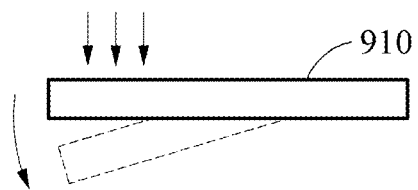
Figure 9B:
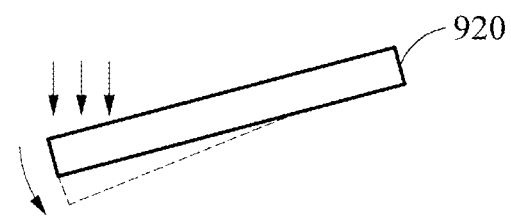

FIGS. 9A and 9B illustrate examples of a condition required to accurately measure a weight of a user based on bending of a neck portion (e.g., neck portions 910 and 920) of a load cell according to an example embodiment. In the example of FIG. 9A, illustrated is a situation in which a bottom plate is disposed on a flat surface, and a force applied to the neck portion 910 by a weight of a user is perpendicular to the neck part 910. In the example of FIG. 9B, illustrated is a situation in which a bottom plate is disposed on a slope, and a force applied to the neck portion 920 by a weight of a user is not perpendicular to the neck portion 920. When the force applied to the neck portion 920 by the weight of the user is not perpendicular to the neck portion 920 as illustrated in FIG. 9B, the neck portion 920 may not be sufficiently bent, and thus the weight of the user may not be accurately measured. Thus, being vertical between a force applied by a weight of a user and a neck portion may be important, and a supporter may be used for this. The supporter will be described in detail with reference to FIGS. 10 and 11.

Figure 10:
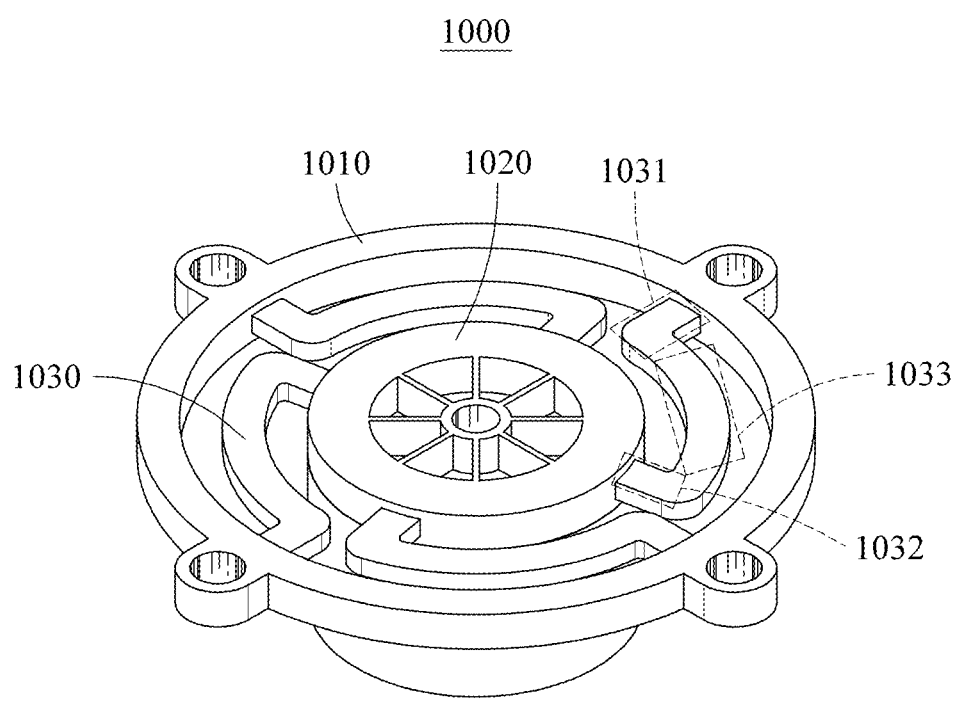

Referring to FIG. 10, a supporter 1000 includes a first portion 1010 connected to a load cell, a second portion 1020 connected to a floor, and a spiral-shaped bridge 1030 configured to connect the first portion 1010 and the second portion 1020. The bridge 1030 may be provided as a plurality of bridges. The bridge 1030 includes a first fixing portion 1031 fixed to the first portion 1010, a second fixing portion 1032 fixed to the second portion 1020, and a connecting portion 1033 configured to connect the first fixing portion 1031 and the second fixing portion 1032 to be in a structure parallel to a circumference of the second portion 1020. That is, the bridge 1030 may protrude in a direction from the first portion 1010 connected to the floor toward the second portion 1020 connected to the load cell, and then be formed in parallel to the circumference of the second portion 1020 to be connected to the second portion 1020.

Using such a structure of the supporter 1000 described in the foregoing, a degree of freedom (DOF) in all directions may be secured such that a force is transferred vertically to a neck portion of the load cell.

Figure 11:
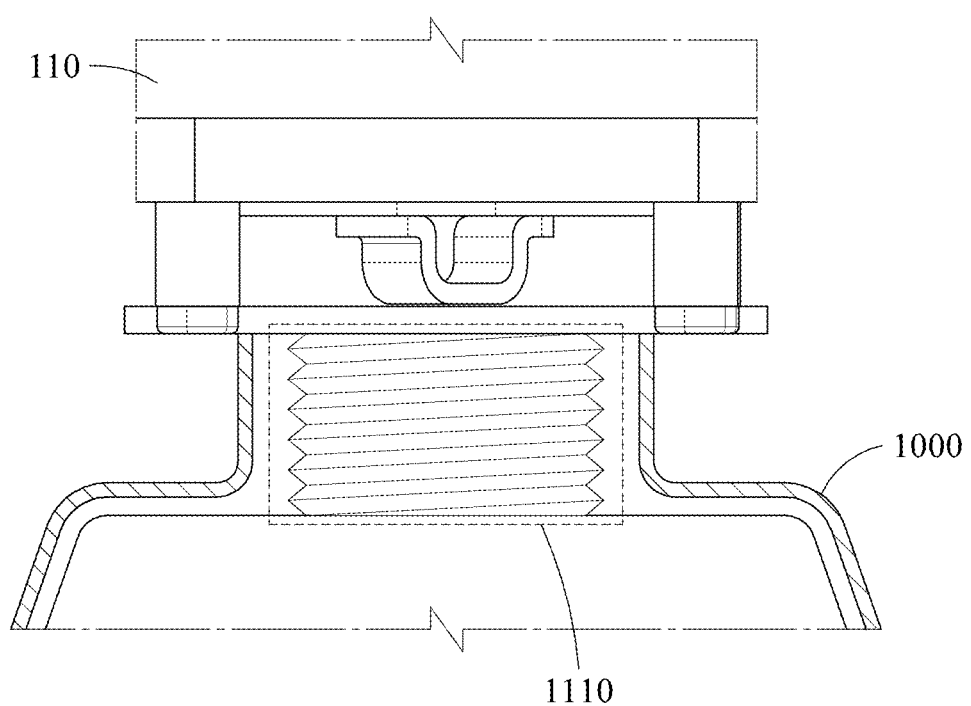

FIG. 11 is a side view of the supporter 1000 connected to a load cell according to an example embodiment. The supporter 1000 may further include a height adjuster 1110. The height adjuster 1110 may be provided in a spiral shape and rotate by a user to adjust a height, and allow a bottom plate to be arranged horizontally.

The units described herein may be implemented using hardware components and software components. For example, the hardware components may include microphones, amplifiers, band-pass filters, audio to digital convertors, non-transitory computer memory and processing devices. A processing device may be implemented using one or more general-purpose or special purpose computers, such as, for example, a processor, a controller and an arithmetic logic unit (ALU), a digital signal processor, a microcomputer, a field programmable gate array (FPGA), a programmable logic unit (PLU), a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a processing device may include multiple processors or a processor and a controller. In addition, different processing configurations are possible, such as parallel processors.

The software may include a computer program, a piece of code, an instruction, or some combination thereof, to independently or collectively instruct or configure the processing device to operate as desired. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. The software and data may be stored by one or more non-transitory computer readable recording mediums. The non-transitory computer readable recording medium may include any data storage device that can store data which can be thereafter read by a computer system or processing device.

The methods according to the above-described example embodiments may be recorded in non-transitory computer-readable media including program instructions to implement various operations of the above-described example embodiments. The media may also include, alone or in combination with the program instructions, data files, data structures, and the like. The program instructions recorded on the media may be those specially designed and constructed for the purposes of example embodiments, or they may be of the kind well-known and available to those having skill in the computer software arts. Examples of non-transitory computer-readable media include magnetic media such as hard disks, floppy disks, and magnetic tape; optical media such as CD-ROM discs, DVDs, and/or Blue-ray discs; magneto-optical media such as optical discs; and hardware devices that are specially configured to store and perform program instructions, such as read-only memory (ROM), random access memory (RAM), flash memory (e.g., USB flash drives, memory cards, memory sticks, etc.), and the like. Examples of program instructions include both machine code, such as produced by a compiler, and files containing higher level code that may be executed by the computer using an interpreter. The above-described devices may be configured to act as one or more software modules in order to perform the operations of the above-described example embodiments, or vice versa.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A height measurer comprising:
   a bottom plate;
   a standing frame connected to the bottom plate to be supported thereby and having a rail on a rear surface thereof;
   a moving portion configured to vertically move the rail;
   a tact switch disposed in at least a portion of the moving portion; and
   a head plate surrounding the standing frame, configured to move vertically along the moving portion, hinge-coupled to the moving portion, and configured to apply a pressing force to the tact switch while being lifted upward upon coming into contact with a head of a user during a height measurement,
   wherein the head plate is a panel having a center of gravity lopsided toward a front portion compared to a rear portion thereof, and is configured to be restored not to press the tact switch by its own weight according to the lopsided center of gravity when the head plate does not touch the user's head and it is not in a state of being lifted upward, and
   wherein a height of the user is measured based on a height of the head plate from which the tact switch is sensed as being pressed.

2. The height measurer of claim 1, wherein the head plate has a curved shape designed to allow a center of gravity to be lopsided.

3. The height measurer of claim 1, wherein a front surface of the standing frame is formed as a flat plate, and the rear surface of the standing frame comprises a groove on which the rail is disposed.

4. The height measurer of claim 1, wherein, while the measurement is not being performed, the head plate is configured to stand by at a first height in a first set state, and to stand by at a second height lower than the first height in a second set state.

5. The height measurer of claim 1, wherein the bottom plate comprises a display configured to display a measurement result which is a result of the measurement performed on the user,
   wherein the display is configured to display the measurement result in a first direction, and then in a second direction different from the first direction when a preset condition is satisfied.

6. The height measurer of claim 5, wherein the preset condition is at least one of a condition that a first threshold time elapses after the tact switch is restored after being pressed, a condition that a second threshold time elapses after the measurement is terminated, a condition that a third threshold time elapses after a weight change is detected as the user steps down from the bottom plate, and a condition that a separate operation command is received.

7. The height measurer of claim 1, further comprising:
- a load cell attached to a rear surface of the bottom plate and configured to measure a weight of the user as a neck portion thereof is bent; and
- a supporter configured to support the bottom plate from a floor and configured to transfer, to the load cell, a pressing force of the user standing on the bottom plate.

8. The height measurer of claim 7, wherein, even when an axial direction in which the supporter stands on the floor and a pressing direction in which the neck portion is pressed by the user do not correspond to each other during the measurement, the supporter is configured to apply a pressure to the load cell in a direction in which the neck portion of the load cell is bent than the axial direction, as a plurality of bridges of the supporter is bent independently from each other.

9. The height measurer of claim 8, wherein each of the bridges of the supporter has a spiral shape that connects, in the supporter, a first portion connected to the load cell and a second portion connected to the floor.

10. The height measurer of claim 9, wherein each of the bridges of the supporter comprises:
- a first fixing portion fixed to the first portion connected to the floor in the supporter;
- a second fixing portion fixed to the second portion connected to the load cell; and
- a connecting portion configured to connect the first fixing portion and the second fixing portion to be in a structure parallel to a circumference of the second portion.

* * * * *